Reissued Aug. 28, 1945

Re. 22,671

UNITED STATES PATENT OFFICE 22,671

SEPARATION OF DIOLEFINS

Rupert C. Morris and Harry de V. Finch, Berkeley, Calif., assignors to Shell Development Company, San Francisco, Calif., a corporation of Delaware No Drawing. Original No. 2,373,329, dated April 10, 1945, Serial No. 404,064, July 25, 1941. Application for reissue May 26, 1945, Serial No. 596,090

9 Claims. (Cl. 260—329)

This invention relates to the separation of diolefins from hydrocarbon mixtures, and more particularly to the separation of isoprene and piperylene from mixtures which are rich in olefins, such as those produced by the vapor-phase cracking of petroleum or petroleum fractions. In one of its more specific embodiments the invention pertains to the separation of isoprene and piperylene from hydrocarbon mixtures rich in olefins, these mixtures boiling substantially close to the boiling temperatures of these diolefins so as to render their recovery by ordinary distillation processes impractical and in some cases substantially impossible. The invention is also directed to a novel compound described hereinbelow.

Both isoprene (2-methyl-butadiene-1,3) and piperylene (pentadiene-1,3) are valuable compounds which may be used for the manufacture of various intermediate, auxiliary and final products for the textile, resin, lacquer, dye-stuff and related industries. For example, both of these compounds are highly suitable for the preparation of products of polymerization. Also, the sulfone derivatives of isoprene and piperylene can be used as intermediate for the manufacture of organic dye-stuffs and textile assistants, some of the reaction products formed from these sulfones being suitable as solvents and softeners.

It is known that hydrocarbon fractions, even when they boil within relatively narrow ranges, consist of a number of different hydrocarbons having different structures, possessing different properties and characteristics, and suitable for different uses. For example, when a hydrocarbon fraction formed by the pyrolysis of hydrocarbons of the type of naphtha, kerosene, stove oil, or the like, is fractionally distilled to recover separately the fraction boiling between about 25° C. and about 50° C. to 55° C., this narrow boiling fraction will predominate in various olefins having five carbon atoms per molecule. Besides the different amylenes (i. e. straight-chain or branched-chain mono-olefins having five carbon atoms per molecule) this fraction will also contain greater or lesser concentrations of isoprene and piperylene, as well as cyclopentadiene. As stated, these diolefins are suitable for various purposes and in various industries, so that their separate recovery from hydrocarbon fractions consisting of or predominating in olefinic hydrocarbons having five carbon atoms per molecule (i. e. $C_5$ fractions) is highly desirable.

It has been previously proposed to separate diolefins from narrow-boiling, olefin-containing or olefin-predominating hydrocarbon fractions. For example, when dealing with narrow-boiling hydrocarbon mixtures containing cyclopentadiene and other diolefins of similar boiling temperatures, it has been proposed to separate the cyclopentadiene therefrom by subjecting such hydrocarbon mixtures, at superatmospheric pressures sufficient to maintain the hydrocarbons in a liquid state, to temperatures of between 40° C. and 170° C., thereby selectively converting the cyclopentadiene to dicyclopentadiene, fractionating the resulting mixture, preferably by distillation under a reduced pressure, to recover the dicyclopentadiene as the bottom fraction, and depolymerizing the separated dicyclopentadiene, for example, by heating it at or near its boiling temperature in a still, preferably with provision for removing and condensing the cyclopentadiene vapors as rapidly as they are formed.

It is also known that acyclic diolefins may be separated from olefinic or olefin-containing mixtures by contacting such mixtures at elevated temperatures and pressures with sulfur dioxide to form the sulfones of these diolefins. These sulfones are then separated from the unreacted hydrocarbons by cooling the reaction mixture to effect the separation of the solid sulfones. The chief difficulty of this method lies in the fact that, unless suitable precautions are taken, instead of forming crystalline or crystallizable sulfones which upon heating readily decompose to yield substantially quantitative amounts of the diolefins, a reaction between the acyclic diolefins and sulfur dioxide tends toward the formation of insoluble amorphous products which do not readily yield the diolefins when subjected to ordinary processes of decomposition. The amorphous compounds are diolefin poly-sulfones, while the crystalline compounds are mono-sulfones, i. e. monomeric diolefin sulfones. In order to prevent the formation of the poly-sulfones, it has been previously proposed to effect the reaction in the presence of oxidation-inhibiting phenolic substances, such as hydroquinone, pyrogallol, pyrocatechol, and the like, or by avoiding the presence of a large excess of the sulfur dioxide in the reaction zone.

In all cases of separation of the acyclic diolefins from hydrocarbon mixtures containing the same, the sulfones formed were separated as a solid crystalline and/or amorphous mass, depending on whether the reaction between the diolefins and the sulfur dioxide produced monomeric or polymeric sulfones, or mixtures thereof. This separation was effected by cooling the reaction mixture substantially to room temperatures, recovering the solid sulfones for instance by filtration, and subsequently decomposing these sulfones to recover the diolefins. If the original hydrocarbon mixture thus treated contained more than one type of diolefins, it was heretofore necessary to subject the diolefins thus recovered from the solid sulfones to a difficult fractionation to obtain the individual diolefins.

It has now been discovered that not all of the sulfones formed by the reaction of acyclic diolefins with sulfur dioxide are solid at or substantially near ordinary temperatures and pressures. It has been particularly found that, whereas the monomeric isoprene sulfone is a normally solid, white crystalline material which melts without decomposition at a temperature of about 64° C., monomeric piperylene sulfone is a normally liquid substance, the physical and chemical characteristics of which are totally different from those of the aforementioned monomeric isoprene sulfone.

In view of the aforementioned discovery, it was found that isoprene and piperylene may be separately and readily recovered from hydrocarbon fractions containing the same, and especially from narrow-boiling fractions predominating in or substantially consisting of five-carbon atom unsaturated hydrocarbons, these acyclic diolefins being obtainable either as such or in the form of their monomeric sulfones. Broadly stated, this is accomplished by reacting the diolefin-containing hydrocarbon fraction with sulfur dioxide under conditions whereby the formation of the monomeric diolefin sulfones is favored, separating these sulfones from the reaction mixture and, after cooling to substantially room temperatures (i. e. between about 15° C. and about 25° C.) or below, separating the solid sulfones from the normally liquid sulfones. These may then be separately decomposed, as by heating, to yield the corresponding acyclic diolefins. This process finds particular use in the separation of isoprene and piperylene from hydrocarbon mixtures containing other olefinic hydrocarbons having five carbon atoms per molecule, such hydrocarbon mixtures boiling in the vicinity of the boiling temperatures of the mentioned $C_5$ acyclic diolefins, thus rendering their separation by ordinary distillation highly difficult, if not totally impossible. On the other hand, since monomeric isoprene sulfone is readily crystallized (by cooling to a temperature below 64° C.), while the monomeric piperylene sulfone is normally liquid, it is possible to form these sulfones by reacting the $C_5$ fraction containing isoprene and piperylene with sulfur dioxide, recovering the sulfones, cooling them to crystallize and separate the isoprene sulfone and then, if desired, decomposing the two sulfones separately, thereby recovering substantially quantitative yields of the acyclic diolefins.

It was also discovered that the rate of addition of sulfur dioxide to various acyclic diolefins, even those having the same number of carbon atoms per molecule, is not the same. For example, when an olefinic fraction boiling between about 32° C. and about 36° C., and containing isoprene as to the only acyclic diolefin therein (this diolefin comprising about 44.3% by weight of the fraction), was treated for about 0.5 hour at a temperature of about 99° C. with sulfur dioxide employed in a 3.86:1 mol ratio, i. e. 3.86 mols of sulfur dioxide per mol of isoprene, the yield of the solid monomeric isoprene sulfone was equal to about 95.5%. On the other hand, when the starting material consisting of an olefinic hydrocarbon fraction boiling between about 41° C. and about 44° C. and consisting of mono-olefins and about 42.8 weight per cent of piperylene, the yield of the monomeric piperylene sulfone, when subjected to the same treatment, was only about 73.3%. In order to raise this yield to 96.3%, it was necessary to continue the heating for about 2 hours. Also, under similar operating conditions, it was necessary to heat a mixture of sulfur dioxide and a butadiene-containing olefinic fraction for about 2½ hours before the monomeric butadiene sulfone yield was equal to 97.1%. Therefore, because of the mentioned difference in the rates of reaction between sulfur dioxide and the various acyclic diolefins, it is possible to obtain concentrated diolefin sulfones or to isolate individual sulfones by regulating the reaction time and, if desired, the quantity of sulfur dioxide added.

According to the process of the present invention, in order to prevent or inhibit the formation of the amorphous insoluble poly-sulfones, the hydrocarbon fraction, prior to its reaction with sulfur dioxide, is first treated to remove any organic peroxides which may be present therein. This is because the presence of the peroxides during the treatment with sulfur dioxide tends to cause the formation of the poly-sulfones. The olefinic hydrocarbons, and particularly the fractions which contain relatively high percentages of diolefins, are quite reactive, and will tend to form organic peroxides even by a mere contact with air at ordinary temperatures and pressures. Therefore, after a hydrocarbon fraction has been treated for the removal or decomposition of the peroxides present therein, it is essential to prevent any further formation of the organic peroxides in the interim between the purification step and the time when the peroxide-free fraction is reacted with sulfur dioxide under conditions favorable to the formation of the monomeric sulfones of the diolefins present therein. This may be effected by reacting the hydrocarbons with the sulfur dioxide substantially immediately after the removal of the peroxides therefrom, by the addition of inhibitors, such as pyrogallol, pyrocatechol, or the like, to the purified hydrocarbons, by storage in an inert atmosphere, or by employing other known means or methods of inhibiting peroxide formation.

Although the mol ratio of the sulfur dioxide to the diolefins may vary within relatively wide limits, in order to recover high yields of the desired monomeric sulfones it is preferable to use the sulfur dioxide in amounts greatly in excess of those necessary for the conversion of the diolefins into the corresponding mono-sulfones. For example, other conditions being maintained by increasing the mol ratio of sulfur dioxide to isoprene from about 2:1 to about 4:1, it is possible to raise the yield of the isoprene sulfone from about 78% to about 99.5%. This increase in the yield of the mono-sulfones is effected without the use of any catalysts and/or restraining agents, the sole requirement being that the diolefin-containing hydrocarbon fraction be free from organic peroxides. This discovery is contrary to the well-accepted opinions to the effect that the use of sulfur dioxide in excess of the amount necessary to combine with the acyclic diolefins tends to form insoluble amorphous addition products (poly-sulfones). Consequently, in order to inhibit the formation of these undesirable by-products, it was heretofore the general practice to avoid the use of large excesses of sulfur dioxide and/or to cause the hydrocarbon mixture to be contacted step-wise with several relatively small amounts or doses of the sulfur dioxide, each of these doses being usually considerably less than one-half of the total weight of the hydrocarbon fraction treated. Such a procedure is generally undesirable because it consumes large periods of time, thereby rendering the process uneconomical. The use of peroxide-free olefins or olefin-containing hydrocarbon fractions allows the use of large excesses of sulfur dioxide without the tendency to form the undesirable poly-sulfones. Such a procedure decreases the overall reaction time and, at the same time, permits the recovery of high yields of the monomeric sulfones of the acyclic diolefins present in the reacting mixture.

In accordance with the present process, it is preferable to effect the addition reaction in the liquid phase, or at least under such conditions of operation that the reactants, namely sulfur dioxide and the acyclic diolefins, are predominantly in the liquid state. In the case of most of the acyclic diolefins, the reaction temperature should be maintained in the neighborhood of 100° C. However, somewhat higher or lower temperatures may also be used. When the operating temperature drops too low, the addition reaction rate becomes so slow as to render the process uneconomical. On the other hand, care should be taken to prevent the use of excessively high temperatures at which substantial decomposition of the sulfones occurs. Also, although the reactants may be at pressures which are only sufficient to maintain them in a liquid state (at the operating temperatures), higher pressures may also be employed. In this connection it must be noted that the reaction pressure is considerably higher than that at which the reactants are introduced into the reaction vessel (e. g. autoclave). This is due to the fact that it is generally preferable to effect this introduction of the reactants at or below ordinary temperatures, whereas the reaction temperature is in the neighborhood of 100° C. As a general rule, the reaction pressures in the autoclave are between about 150 lbs. per sq. in. and about 200 lbs. per sq. in., or higher, depending in part on the type of diolefins treated.

The invention is further illustrated by the following specific examples, it being understood that there is no intention to be limited by any details thereof, since many apparent variations may be made.

*Example I*

A freshly distilled, peroxide-free hydrocarbon fraction boiling between 28° C. and 55° C., and produced by thermal cracking of the second cut straight-run gasoline, was employed. This fraction (which predominated in olefins having five carbon atoms per molecule) upon analysis was found to contain about 36 weight percent of acyclic diolefins. The hydrocarbon fraction and sulfur dioxide were then separately liquefied by chilling and maintaining them at a superatmospheric pressure of about 20 lbs. per sq. in. gage. The reactants were then introduced into an evacuated bomb reactor which was chilled by means of a solid carbon dioxide bath. Approximately 1.58 mols of liquid sulfur dioxide and about 0.613 mol of the above hydrocarbon fraction (which contained about 0.355 mol of acyclic diolefins) were thus introduced into the reactor. The mol ratio of the sulfur dioxide to the acyclic diolefins was thus equal to 4.4:1. The reactor was then closed and placed into boiling water so as to maintain the reaction temperature within the reactor at between about 99° C. and about 100° C., the pressure within the reactor rising to about 150 to 175 lbs. per sq. in. The reaction was continued for a period of 2 hours, after which the unreacted gases were released while the liquid fraction (about 0.272 mol) was conveyed to a container which was then cooled to a temperature of about −13° C. This cooling caused the formation of large white crystals which were separated from the remaining liquid fraction by filtration by suction. The crystals, having a melting point of 64° C., were readily soluble in most solvents, and upon analysis showed that they were the crystals of isoprene mono-sulfone. The remaining liquid fraction was then found to consist of piperylene mono-sulfone which is believed to have the structural formula

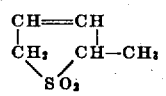

Analyses and determination of the physical contents of a sample of this mono-sulfone gave the following results:

| | Found | Calculated |
|---|---|---|
| Density, *d*-20/4 | 1.2220 | |
| Refractive index, N-20/D | 1.4945 | |
| Carbon ... percent | 47.1 | 45.5 |
| Hydrogen ... do | 6.41 | 6.6 |
| Sulfur ... do | 23.1 | 24.2 |
| Bromine number | 122 | 121 |

The material was readily soluble in ethyl alcohol, acetone, carbon tetrachloride and acetic acid.

The above reaction between the diolefin-containing hydrocarbon fraction and sulfur dioxide resulted in a 76.5% yield of diolefin sulfones, of which about 56% by weight consisted of the above novel, normally liquid monomeric piperylene sulfone.

In order to recover substantially pure piperylene and isoprene, the above sulfones were separately decomposed by distillation at atmospheric pressure and at temperatures of between about 120° C. and about 130° C. The overhead gaseous fractions were conveyed through alkali scrubbers containing a 10% aqueous solution of sodium hydroxide. This removed the liberated sulfur dioxide. The remaining gases were then condensed, and were found to be substantially pure piperylene and isoprene, respectively.

*Example II*

A freshly distilled, peroxide-free hydrocarbon fraction obtained in the same manner as that used in the previous example, and having the same percentages of the different mono- and diolefins, was reacted with liquid sulfur dioxide under the same conditions as those employed in Example I, except that the reaction time was shortened to about ½ hour. The total yield of sulfones dropped to about 70%, these sulfones having a greater percentage of isoprene mono-sulfone. The unreacted gases were then again treated with an excess of sulfur dioxide to yield an additional amount of a diolefin sulfone which was found to be practically pure piperylene sulfone.

The above examples clearly show that isoprene and piperylene (as well as their respective mono-sulfones) may be separately recovered from hydrocarbon mixtures containing the same by subjecting such mixtures, at superatmospheric pressure and temperatures of about 100° C., to the action of sulfur dioxide (preferably employed in a large excess over the amount necessary to form the mono-sulfones), by cooling the reaction mixture to effect the solidification of the isoprene sulfone, and by separating the same from the normally liquid piperylene mono-sulfone by any known means, such as filtration, centrifuging, decanting, or the like. If desired, the respective sulfones may then be decomposed to yield substantially pure isoprene and piperylene, respectively.

The present process is also applicable to the separation of substantially pure piperylene from hydrocarbon fractions boiling within a very narrow boiling range and containing mono-olefins and piperylene as the only diolefin. The following example shows the specific procedure:

*Example III*

A freshly distilled, peroxide-free hydrocarbon fraction boiling between 41° C. and 44° C., produced by straight distillation of a product formed by cracking second cut straight-run gasoline, was employed. This fraction contained about 42.8 weight per cent of piperylene. The formation of the sulfone was effected according to the process described in Example I, the sulfur dioxide being used in a mol ratio of 4:1 and the reaction period being about 2 hours. After removal of the unreacted products, the piperylene sulfone was obtained in a yield of 96.3%. This mono-sulfone was then decomposed by heating to 125° C.–130° C. The diolefin fraction thus produced, after separation of the liberated sulfur dioxide, analyzed 99% pure piperylene.

The above examples disclose the use of peroxide-free hydrocarbon fractions. As noted above, the presence of organic peroxides under the reaction conditions tends to form diolefin poly-sulfones which are difficult to decompose. The mere addition of inhibitors of the type of pyrogallol is insufficient since they merely inhibit further formation of the peroxides and do not decompose those already present in the hydrocarbon mixtures treated. Therefore, in order to produce high yields of the desirable mono-sulfones, it is advantageous to destroy these peroxides, for example, by distillation, cracking, or by otherwise destroying and/or removing the organic peroxides from the hydrocarbon fraction to be subjected to the action of sulfur dioxide.

Although the process is particularly adapted to the separation of isoprene and piperylene from hydrocarbon mixtures containing the same, it also finds utility in the treatment of hydrocarbon fractions containing other acyclic diolefins. For example, it was found that some conjugated diolefins having six carbon atoms per molecule form normally liquid mono-sulfones, so that they may be thus separated from the other normally solid sulfones. Instead of separating the sulfones prior to their decomposition, all of the mono-sulfones may be decomposed in toto, and the resulting diolefin fraction may then be treated, for instance, by careful fractionation to recover the individual diolefins. If a $C_5$ fraction contains cyclopentadiene (which apparently does not form the mono-sulfone), it may be advisable to separate this diolefin for instance by the above described method of polymerization to dicyclopentadiene, followed by fractionation to recover this polymer as a bottom fraction, and its decomposition back to cyclopentadiene.

We claim as our invention:

1. A process for recovering isoprene and piperylene from hydrocarbon mixtures containing same which comprises subjecting a peroxide-free hydrocarbon fraction predominating in olefins having five carbon atoms per molecule and containing isoprene and piperylene, to the action of sulfur dioxide at an elevated temperature in the neighborhood of 100° C. and under a superatmospheric pressure sufficient to maintain the reactants in the liquid state, recovering the resultant addition products, cooling said addition products to crystallize the isoprene sulfone present therein, separating the crystalline isoprene sulfone from the remaining liquid comprising piperylene mono-sulfone, subjecting the isoprene sulfone and the piperylene sulfone to elevated temperatures to effect their decomposition, and separating sulfur dioxide from the resultant reaction products thereby producing high yields of substantially pure isoprene and piperylene, respectively.

2. The process according to claim 1, wherein the sulfur dioxide employed for the production of the sulfones is used in a quantity in excess of that necessary to combine with the acyclic diolefins present in the hydrocarbon fraction treated.

3. A process for recovering isoprene and piperylene from hydrocarbon mixtures containing same which comprises contacting a peroxide-free hydrocarbon fraction predominating in olefins having five carbon atoms per molecule and containing isoprene and piperylene, with sulfur dioxide employed in a quantity in excess of that necessary to combine with said diolefins, subjecting the mixture to an elevated temperature in the neighborhood of 100° C. and to a superatmospheric pressure sufficient to maintain the reactants in the liquid state for a period of time sufficient to effect the addition reaction, recovering the resultant addition products, cooling said products to crystallize the isoprene sulfone, separating the remaining liquid comprising piperylene mono-sulfone, and separately decomposing said sulfones to recover high yields of substantially pure isoprene and piperylene, respectively.

4. The process according to claim 3, wherein the hydrocarbon fraction, substantially immediately prior to the reaction thereof with sulfur dioxide, is subjected to distillation to separate from said fraction any organic peroxides which may be present therein.

5. A process for producing and recovering monomeric isoprene and piperylene sulfones which comprises reacting a peroxide-free hydrocarbon fraction predominating in mono-olefins and diolefins having five carbon atoms per molecule, with sulfur dioxide employed in an amount greatly in excess of that necessary to combine with said acyclic diolefins, effecting the reaction at a temperature in the neighborhood of 100° C., under a superatmospheric pressure and for a period of time sufficient to effect the addition reaction, separating the resultant addition products, cooling said addition products to crystallize the formed isoprene mono-sulfone, and separating said crystalline isoprene sulfone from the remaining liquid fraction comprising monomeric piperylene sulfone.

6. The process according to claim 5 wherein the addition products obtained from the interaction of the acylic diolefins and sulfur dioxide are cooled to a temperature below about 15° C. to effect a complete crystallization of the isoprene sulfone present therein.

7. A process for recovering substantially pure piperylene from hydrocarbon mixtures containing said acyclic diolefin, isoprene and other hydrocarbons of a greater degree of saturation, which comprises subjecting said hydrocarbon mixture to distillation to recover a peroxide-free fraction, reacting said fraction with sulfur dioxide at an elevated temperature and a superatmospheric pressure sufficient to maintain the reactants in the liquid state, separating the addition products comprising isoprene and piperylene sulfones, cooling said mixture to crystallize isoprene sulfone, separating said crystalline mass from the remaining liquid comprising piperylene sulfone, and decomposing said liquid sulfone to recover substantially pure piperylene.

8. A process for producing and recovering monomeric isoprene and piperylene sulfones which comprises reacting sulfur dioxide with a peroxide-free hydrocarbon fraction containing isoprene, piperylene and other hydrocarbons of a greater degree of saturation, effecting the reaction at an elevated temperature and superatmospheric pressure sufficient to maintain the reactants substantially in the liquid state, separating the resultant addition products formed by the addition of the sulfur dioxide to isoprene and piperylene, cooling them to crystallize the isoprene sulfone, and separating it from the remaining liquid fraction comprising piperylene sulfone.

9. A process for producing and recovering monomeric piperylene sulfones which comprises reacting sulfur dioxide with a hydrocarbon fraction containing piperylene and other hydrocarbons boiling close to the boiling temperature of piperylene, effecting the reaction at an elevated temperature and a superatmospheric pressure to effect an addition reaction between sulfur dioxide and diolefins, separating the addition products from the unreacted products, cooling said products to substantially room temperature to effect the crystallization of some of the sulfones, and separating the crystalline mass from the remaining liquid fraction comprising monomeric piperylene sulfone.

RUPERT C. MORRIS.
HARRY DE V. FINCH.